(12) United States Patent
Aiba et al.

(10) Patent No.: US 9,657,325 B2
(45) Date of Patent: May 23, 2017

(54) GLUCOSE DEHYDROGENASE

(71) Applicant: TOYOBO CO., LTD., Osaka-shi, Osaka (JP)

(72) Inventors: Hiroshi Aiba, Tsuruga (JP); Yosuke Sumida, Tsuruga (JP); Yasuhiro Yamazaki, Tsuruga (JP); Yuu Utashima, Tsuruga (JP); Takahide Kishimoto, Tsuruga (JP)

(73) Assignee: Toyobo Co., Ltd., Osaka (JP)

( * ) Notice: Subject to any disclaimer, the term of this patent is extended or adjusted under 35 U.S.C. 154(b) by 0 days.

(21) Appl. No.: 15/134,684

(22) Filed: Apr. 21, 2016

(65) Prior Publication Data

US 2016/0265021 A1 Sep. 15, 2016

Related U.S. Application Data

(63) Continuation-in-part of application No. PCT/JP2014/077223, filed on Oct. 10, 2014.

(30) Foreign Application Priority Data

Oct. 21, 2013 (JP) .................. 2013-218308

(51) Int. Cl.
 C12Q 1/00 (2006.01)
 C12N 9/04 (2006.01)
 G01N 27/327 (2006.01)
(52) U.S. Cl.
 CPC ........... *C12Q 1/006* (2013.01); *C12N 9/0006* (2013.01); *G01N 27/3271* (2013.01); *C12Y 101/05* (2013.01)

(58) Field of Classification Search
 None
 See application file for complete search history.

(56) References Cited

U.S. PATENT DOCUMENTS

| 7,871,805 | B2 | 1/2011 | Aiba et al. |
| 8,445,246 | B2 | 5/2013 | Tajima et al. |
| 2006/0063217 | A1 | 3/2006 | Omura et al. |
| 2008/0014612 | A1* | 1/2008 | Tsuji ............ C12N 9/0006 435/69.1 |
| 2008/0020426 | A1* | 1/2008 | Aiba ............ C12N 9/0006 435/69.1 |
| 2009/0176262 | A1 | 7/2009 | Omura et al. |

(Continued)

FOREIGN PATENT DOCUMENTS

| JP | 4292486 B2 | 7/2009 |
| JP | 4348563 B3 | 10/2009 |

(Continued)

OTHER PUBLICATIONS

Japanese Patent Office, International Search Report in International Patent Application No. PCT/JP2014/077223 (Jan. 6, 2015).

*Primary Examiner* — Robert Mondesi
*Assistant Examiner* — Richard Ekstrom
(74) *Attorney, Agent, or Firm* — Leydig, Voit & Mayer, Ltd.

(57) ABSTRACT

Provided is a flavin adenine dinucleotide-dependent glucose dehydrogenase comprising a polypeptide having an amino acid sequence with 78% or more identity to the amino acid sequence of SEQ ID NO: 3, and having glucose dehydrogenase activity.

17 Claims, 2 Drawing Sheets

(56) References Cited

U.S. PATENT DOCUMENTS

| | | | |
|---|---|---|---|
| 2009/0259024 A1* | 10/2009 | Tsuji | C12N 9/0006 530/350 |
| 2010/0297743 A1 | 11/2010 | Omura et al. | |
| 2011/0020851 A1* | 1/2011 | Aiba | C12N 9/0006 435/14 |
| 2012/0122130 A1* | 5/2012 | Omura | C12N 9/0004 435/14 |
| 2012/0171708 A1* | 7/2012 | Kawaminami | C12N 9/0006 435/14 |
| 2013/0183716 A1* | 7/2013 | Kawano | C12N 9/0006 435/90 |
| 2013/0309750 A1 | 11/2013 | Tajima et al. | |
| 2014/0154777 A1 | 6/2014 | Sumida et al. | |
| 2014/0287445 A1 | 9/2014 | Tajima et al. | |
| 2014/0287478 A1* | 9/2014 | Sumida | C12Q 1/006 435/190 |
| 2015/0031059 A1 | 1/2015 | Sumida et al. | |
| 2015/0111280 A1* | 4/2015 | Sumida | C12N 9/0006 435/190 |
| 2015/0240216 A1* | 8/2015 | Yamazaki | C12Q 1/54 435/190 |
| 2015/0267178 A1 | 9/2015 | Ozawa et al. | |

FOREIGN PATENT DOCUMENTS

| | | |
|---|---|---|
| JP | 4494978 B2 | 6/2010 |
| JP | 4648993 B2 | 3/2011 |
| JP | 2013-081399 A | 5/2013 |
| WO | WO 2004/058958 A1 | 7/2004 |
| WO | WO 2012/073987 A1 | 6/2012 |
| WO | WO 2012/169512 A1 | 12/2012 |
| WO | WO 2013/022074 A1 | 2/2013 |
| WO | WO 2013/118798 A1 | 8/2013 |
| WO | WO 2014/045912 A1 | 3/2014 |

\* cited by examiner

SEQUENCE LISTING

<160> NUMBER OF SEQ ID NOS: 3

<210> SEQ ID NO 1
<211> LENGTH: 737
<212> TYPE: DNA
<213> ORGANISM: Aspergillus sp. RD009469

<400> SEQUENCE: 1

```
catcctggag ctgtctggaa ttggcaaccc gaacgtcctg aaaaagcaca acatccctgt      60
caaggtcgac ttgcccaccg tcggcgaaaa cctccaggat cagacaaata gcccacatgga    120 tgcggctagc aacagctccc tttctggtgg aaagcccgtt gcctaccccg acatctacga    180
tgttctcggc gacgaggcag aggcggtagc aaagaagctc cgcgccaatc tgaagaagta    240
cgcagaagag actgccaagg caaatggtaa tatcatgaag gtgtccgatc ttgaacgtct    300
gtttgaagtg cagtatgatc tcatcttcaa ggagaggacc cccgtcgctg aagttctcag    360
ctacgctgcc ggcaagtctc tgtccacgga attctggtcc ctgttgcctt tctcccgtgg    420
aagcgttcac attgcgtctt ccaacccgaa acagttcccc acaatcaacc ccaactactt    480
catgtttgaa tgggatgttg agagctacgt tgcagttgcg cggtacattc gtcgctcgta    540
tgagagcgcc cctcttaaca ctcttgttaa ggagtctact ccgggcctca agactattcc    600
gcagaatgcc tctgtggagc aatggaagga gtggttctt aagggtaact gtaagtttgc      660
caaaatctcg catatcgccg catatatacc ggtgagcatc tttctaacta tcattcagat    720
cgctccaact tccaccc                                                     737
```

<210> SEQ ID NO 2
<211> LENGTH: 1776
<212> TYPE: DNA
<213> ORGANISM: Aspergillus sp. RD009469

<400> SEQUENCE: 2

```
atgtttggca aactcacgtt tcttagtgca ttgtcactgg caattgccgc tccctggacg      60
cagtccgcat cgtctgacta tgattacatc gtcattggag gcgggactag cggccttgct    120
gttgcgaatc gtttgtccga ggatccgaac gtgaatgtgc ttattgtcga ggctggcggt    180
tccgttttga caaccctaa cgtgacgaac gtcaatggct atggtcgttc ttttggcaca      240
gagatcgact ggcagtacca gtctgtcaac cagacccatg ctggaaatgt tcgtcaggtc    300
cttcgtgctg gaaaggcgct ggccggaacc agtgccatca acggcatggc ttataccgt      360 gctgaggatg tccagatcga cgcgtgggaa accattggta atgagggatg gacctggaag    420
aacctcttcc cttactacct gaagagcgag aacttcaccc gcctaccgga gatccaactc    480
aagctaggag cctcgtacaa acccgtatac cacggcgaaa agggcccct cgacgtttcc    540 ttcaccaaga tcgaatccaa caacctgacc acctacctca accgcacctt cgagggcatg    600
ggtctcccat gggcagaaga tatcggcggc gggaagatgc gtggcttcaa catcttcccc    660
tccacagtca accctacgga gtatgttcgt gaggatgctg ctcgtgcata ctactggccc    720
ttcgagtccc gcaagaacct tcatgtcctc ctcaatacct tgccaatcg cattgtgtgg      780 gctgagggag ccgtggtag tgctgctact gccagcggcg tcgaagtcgc ctcaaagaac    840
ggcactgtca gcgtcgtcaa agcgagtaag gaagtgatcg tgtccgctgg tgctctgaag    900
tctcctgcca tcctggagct gtctggaatt ggcaacccga acgtcctgaa aaagcacaac    960
atccctgtca aggtcgactt gcccaccgtc ggcgaaaacc tccaggatca gacaaatagc   1020
cacatggatg cggctagcaa cagctccctt tctggtggaa agcccgttgc ctaccccgac   1080
```

```
atctacgatg ttctcggcga cgaggcagag gcggtagcaa agaagctccg cgccaatctg   1140
aagaagtacg cagaagagac tgccaaggca aatggtaata tcatgaaggt gtccgatctt   1200
gaacgtctgt ttgaagtgca gtatgatctc atcttcaagg agaggacccc cgtcgctgaa   1260
gttctcagct acgctgccgg caagtctctg tccacggaat tctggtccct gttgcctttc   1320
tcccgtggaa gcgttcacat tgcgtcttcc aacccgaaac agttccccac aatcaacccc   1380
aactacttca tgtttgaatg ggatgttgag agctacgttg cagttgcgcg gtacattcgt   1440
cgctcgtatg agagcgcccc tcttaacact cttgttaagg agtctactcc gggcctcaag   1500
actattccgc agaatgcctc tgtggagcaa tggaaggagt ggttcttta aggtaactat   1560 cgctccaact tccaccctgt cggtactgcc gctatgatgc cccgtgccat gggtggtgtt   1620
atcgacaacc gcctcaaggt gtacggcact tctaatgttc ggggttgtgga cgcctcctcc   1680 ctgccctacc aggtctgtgg tcatctcgtg agcaccctgt acgctcttgc ggaacgggct   1740
gccgatttca tcaaggagga tgtcgctagt ctctag                             1776
```

<210> SEQ ID NO 3
<211> LENGTH: 591
<212> TYPE: PRT
<213> ORGANISM: Aspergillus sp. RD009469

<400> SEQUENCE: 3

```
Met Phe Gly Lys Leu Thr Phe Leu Ser Ala Leu Ser Leu Ala Ile Ala
1               5                   10                  15

Ala Pro Trp Thr Gln Ser Ala Ser Ser Asp Tyr Asp Tyr Ile Val Ile
            20                  25                  30

Gly Gly Gly Thr Ser Gly Leu Ala Val Ala Asn Arg Leu Ser Glu Asp
        35                  40                  45

Pro Asn Val Asn Val Leu Ile Val Glu Ala Gly Gly Ser Val Leu Asn
    50                  55                  60

Asn Pro Asn Val Thr Asn Val Asn Gly Tyr Gly Arg Ser Phe Gly Thr
65                  70                  75                  80

Glu Ile Asp Trp Gln Tyr Gln Ser Val Asn Gln Thr His Ala Gly Asn
                85                  90                  95

Val Arg Gln Val Leu Arg Ala Gly Lys Ala Leu Ala Gly Thr Ser Ala
            100                 105                 110

Ile Asn Gly Met Ala Tyr Thr Arg Ala Glu Asp Val Gln Ile Asp Ala
        115                 120                 125

Trp Glu Thr Ile Gly Asn Glu Gly Trp Thr Trp Lys Asn Leu Phe Pro
    130                 135                 140

Tyr Tyr Leu Lys Ser Glu Asn Phe Thr Arg Pro Thr Glu Ile Gln Leu
145                 150                 155                 160

Lys Leu Gly Ala Ser Tyr Lys Pro Val Tyr His Gly Glu Lys Gly Pro
                165                 170                 175

Leu Asp Val Ser Phe Thr Lys Ile Glu Ser Asn Leu Thr Thr Tyr
            180                 185                 190

Leu Asn Arg Thr Phe Glu Gly Met Gly Leu Pro Trp Ala Glu Asp Ile
        195                 200                 205

Gly Gly Gly Lys Met Arg Gly Phe Asn Ile Phe Pro Ser Thr Val Asn
    210                 215                 220

Pro Thr Glu Tyr Val Arg Glu Asp Ala Ala Arg Ala Tyr Tyr Trp Pro
225                 230                 235                 240
```

-continued

```
Phe Glu Ser Arg Lys Asn Leu His Val Leu Leu Asn Thr Phe Ala Asn
                245                 250                 255
Arg Ile Val Trp Ala Glu Gly Ala Gly Gly Ser Ala Ala Thr Ala Ser
                260                 265                 270
Gly Val Glu Val Ala Ser Lys Asn Gly Thr Val Ser Val Val Lys Ala
                275                 280                 285
Ser Lys Glu Val Ile Val Ser Ala Gly Ala Leu Lys Ser Pro Ala Ile
    290                 295                 300
Leu Glu Leu Ser Gly Ile Gly Asn Pro Asn Val Leu Lys His Asn
305                 310                 315                 320
Ile Pro Val Lys Val Asp Leu Pro Thr Val Gly Glu Asn Leu Gln Asp
                325                 330                 335
Gln Thr Asn Ser His Met Asp Ala Ala Ser Asn Ser Ser Leu Ser Gly
                340                 345                 350
Gly Lys Pro Val Ala Tyr Pro Asp Ile Tyr Asp Val Leu Gly Asp Glu
                355                 360                 365
Ala Glu Ala Val Ala Lys Lys Leu Arg Ala Asn Leu Lys Lys Tyr Ala
    370                 375                 380
Glu Glu Thr Ala Lys Ala Asn Gly Asn Ile Met Lys Val Ser Asp Leu
385                 390                 395                 400
Glu Arg Leu Phe Glu Val Gln Tyr Asp Leu Ile Phe Lys Glu Arg Thr
                405                 410                 415
Pro Val Ala Glu Val Leu Ser Tyr Ala Ala Gly Lys Ser Leu Ser Thr
                420                 425                 430
Glu Phe Trp Ser Leu Leu Pro Phe Ser Arg Gly Ser Val His Ile Ala
                435                 440                 445
Ser Ser Asn Pro Lys Gln Phe Pro Thr Ile Asn Pro Asn Tyr Phe Met
450                 455                 460
Phe Glu Trp Asp Val Glu Ser Tyr Val Ala Val Ala Arg Tyr Ile Arg
465                 470                 475                 480
Arg Ser Tyr Glu Ser Ala Pro Leu Asn Thr Leu Val Lys Glu Ser Thr
                485                 490                 495
Pro Gly Leu Lys Thr Ile Pro Gln Asn Ala Ser Val Glu Gln Trp Lys
                500                 505                 510
Glu Trp Phe Phe Lys Gly Asn Tyr Arg Ser Asn Phe His Pro Val Gly
    515                 520                 525
Thr Ala Ala Met Met Pro Arg Ala Met Gly Gly Val Ile Asp Asn Arg
                530                 535                 540
Leu Lys Val Tyr Gly Thr Ser Asn Val Arg Val Val Asp Ala Ser Ser
545                 550                 555                 560
Leu Pro Tyr Gln Val Cys Gly His Leu Val Ser Thr Leu Tyr Ala Leu
                565                 570                 575
Ala Glu Arg Ala Ala Asp Phe Ile Lys Glu Asp Val Ala Ser Leu
                580                 585                 590
```

GLUCOSE DEHYDROGENASE

CROSS-REFERENCE TO RELATED APPLICATIONS

This patent application is a continuation-in-part of International Patent Application No. PCT/JP2014/077223, filed Oct. 10, 2014, which claims the benefit of Japanese Patent Application No. 2013-218308, filed on Oct. 21, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 8,775 bytes ASCII (Text) file named "723400SequenceListing.txt," created Apr. 19, 2016.

TECHNICAL FIELD

The present invention relates to a reagent for measuring glucose concentration and glucose dehydrogenase that can be used for glucose sensors. The present invention also relates to a method for producing the enzyme and to a composition for quantifying glucose and a glucose sensor, both of which use the enzyme.

BACKGROUND ART

Flavin adenine dinucleotide (FAD)-dependent glucose dehydrogenase (EC1.1.99.10; hereinafter, glucose dehydrogenase is also referred to as "GDH," and FAD-dependent glucose dehydrogenase as "FAD-GDH") is an enzyme that is mainly used for blood glucose concentration measurement and catalyzes the following reaction.

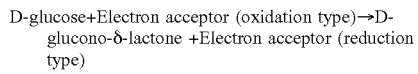

Glucose oxidase is also known as an enzyme for quantifying blood glucose. However, this enzyme is said to have a problem in that glucose concentration measurement using glucose oxidase is affected by the concentration of dissolved oxygen because this enzyme may use molecular oxygen as an electron acceptor. Since glucose dehydrogenase is not influenced by such dissolved oxygen, it has been used as the main enzyme for glucose sensors in recent years. GDH includes FAD-dependent GDH, pyrroloquinoline quinone (PQQ)-dependent GDH, and NAD(P)-dependent GDH. PQQ-dependent GDH, such as *Acinetobacter baumannii*-derived PQQ-dependent GDH, has a problem with substrate specificity in that PQQ-dependent GDH is as reactive with maltose as it is with glucose. Examples of known NAD(P)-dependent GDH include *Bacillus subtilis*-derived NAD(P)-dependent GDH, *Bacillus megaterium*-derived NAD(P)-dependent GDH, *Thermoproteus* sp.-derived NAD(P)-dependent GDH, and the like. NAD(P)-dependent GDH has stricter substrate specificity than PQQ-dependent GDH. However, NAD(P)-dependent GDH is not necessarily useful since NAD(P), a coenzyme, needs to be added separately, thus requiring high costs in the production of reagents for quantifying glucose or sensors, as well as complexity in quality control. In that regard, FAD-GDH, such as FAD-GDH derived from the genus *Aspergillus*, is a coenzyme-bound type and has high substrate specificity; therefore, FAD-GDH has been found useful in recent years.

The production of glucose sensors involves the step of evaporating a GDH solution to dryness on a reaction layer. Attempts are often made to improve the production efficiency by performing heat treatment at 50° C. or more in this step to enhance the efficiency of evaporation to dryness. Although the heat treatment is effective for the production efficiency, proteins are generally known to be denatured by heat, and this risk increases especially in enzymes that have low thermal stability.

Moreover, usually, sensor strips after production are guaranteed for a maximum of two years at about room temperature. However, it is rare for general users using a glucose sensor to store sensor strips with strict temperature control. In particular, considering the situations in which summer temperatures are 35° C. or more, or sometimes exceed 40° C., it is easy to anticipate that high stability of the enzyme itself is desired. Enzymes having excellent thermal stability have commonly stable three-dimensional structures and can be said to be more suitable for long-term storage in harsh conditions.

Examples of known FAD-GDH include those derived from the genus *Penicillium* (Patent Literature 1), the genus *Aspergillus* (e.g., Patent Literature 2 and 3), the genus *Mucor* (e.g., Patent Literature 4 and 5), and the like. The upper limits of the heat resistance of all these enzymes in an aqueous solution are about 50° C. to 55° C., which are insufficient. Patent Literature documents 6 and 7 disclose an example in which the thermal stability of FAD-GDH was improved by using protein engineering technology. However, improvement in stability attained by modification using protein engineering technology has a limit, and thus high stability of the original wild-type enzyme is important.

None of the enzymes disclosed in the patent literature above withstands heat treatment at 60° C. to 65° C., and thus further improvement in stability is needed.

CITATION LIST

Patent Literature

PTL 1: U.S. Pat. No. 7,871,805
PTL 2: JP4494978B
PTL 3: JP4292486B
PTL 4: JP4648993B
PTL 5: WO2013/118798
PTL 6: JP4348563B
PTL 7: WO2012/169512

SUMMARY OF INVENTION

Technical Problem

An object of the present invention is to provide FAD-GDH having high stability in the step of producing glucose sensors and in storage after production.

Solution to Problem

The present inventors conducted extensive research to achieve the above object and found novel FAD-GDH having thermal stability that is higher than that of conventionally known FAD-GDH. The present invention has thus been accomplished.

Specifically, the present invention includes the following embodiments.

Item 1.

A flavin adenine dinucleotide-dependent glucose dehydrogenase having the following properties (A) to (B):

(A) Action: the flavin adenine dinucleotide-dependent glucose dehydrogenase catalyzes a reaction in which D-glucose is oxidized in the presence of an electron acceptor to produce D-glucono-δ-lactone;

(B) Molecular weight: the molecular weight of the polypeptide chain portion of the protein measured by SDS-polyacrylamide electrophoresis is 65000;

(C) Thermal stability: the residual activity after treatment at 60° C. for 15 minutes is 85% or more, the residual activity after treatment at 65° C. for 15 minutes is 50% or more, and the residual activity after treatment at 70° C. for 15 minutes is 10% or more;

(D) Optimum reaction pH: 7.0; and (E) Substrate specificity:

the reactivity to maltose is 2% or less based on the reactivity to D-glucose taken as 100%, the reactivity to D-galactose is 2% or less based on the reactivity to D-glucose taken as 100%, and the reactivity to D-xylose is 10% or less based on the reactivity to D-glucose taken as 100%.

Item 2.

A flavin adenine dinucleotide-dependent glucose dehydrogenase having the following properties (A) to (C):

(A) Amino acid sequence: the flavin adenine dinucleotide-dependent glucose dehydrogenase has an amino acid sequence with 78% or more identity to the amino acid sequence of SEQ ID NO: 3;

(B) Action: the flavin adenine dinucleotide-dependent glucose dehydrogenase catalyzes a reaction in which D-glucose is oxidized in the presence of an electron acceptor to produce D-glucono-δ-lactone; and (C) Thermal stability: the residual activity after treatment at 60° C. for 15 minutes is 85% or more, the residual activity after treatment at 65° C. for 15 minutes is 50% or more, and the residual activity after treatment at 70° C. for 15 minutes is 10% or more.

Item 3.

The flavin adenine dinucleotide-dependent glucose dehydrogenase according to Item 1 or 2, which is derived from a filamentous fungus of the genus *Aspergillus*.

Item 4.

The flavin adenine dinucleotide-dependent glucose dehydrogenase according to Item 3, wherein the filamentous fungus of the genus *Aspergillus* is *Aspergillus* sp. RD009469 strain.

Item 5.

A method for producing the flavin adenine dinucleotide-dependent glucose dehydrogenase according to any one of Items 1 to 4, the method comprising culturing, in a nutrient medium, a microorganism that produces the flavin adenine dinucleotide-dependent glucose dehydrogenase according to any one of Items 1 to 4 and collecting a protein having glucose dehydrogenase activity.

Item 6.

A glucose assay kit comprising the flavin adenine dinucleotide-dependent glucose dehydrogenase according to any one of Items 1 to 4.

Item 7.

A glucose sensor comprising the flavin adenine dinucleotide-dependent glucose dehydrogenase according to any one of Items 1 to 4.

Item 8.

A method for quantifying glucose, the method using the flavin adenine dinucleotide-dependent glucose dehydrogenase according to any one of items 1 to 4.

Advantageous Effects of Invention

The present invention makes it possible to provide glucose dehydrogenase that has high thermal stability and a low risk of deactivation during or after the production of glucose sensors.

DESCRIPTION OF EMBODIMENTS (1) FAD-GDH

Figure 1:
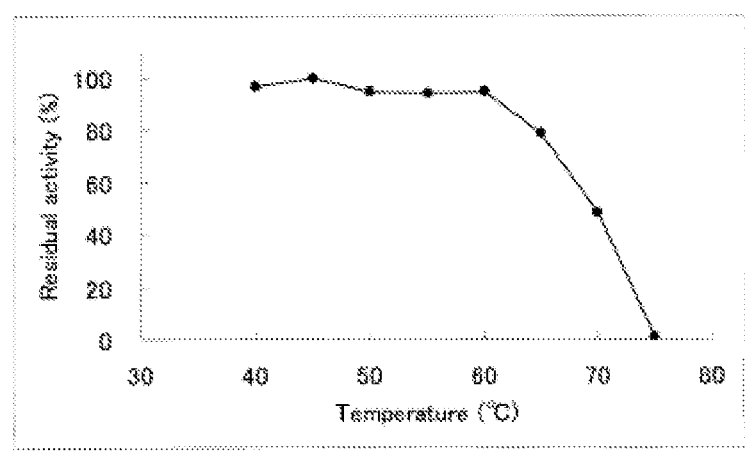
FIG. 1 shows the residual activity at each temperature of treatment for FAD-GDH derived from *Aspergillus* sp. RD009469 strain.

An embodiment of the present invention is a flavin adenine dinucleotide-dependent glucose dehydrogenase (FAD-GDH) having the following properties (A) to (E):

(A) Action: the FAD-GDH catalyzes a reaction in which D-glucose is oxidized in the presence of an electron acceptor to produce D-glucono-δ-lactone;

(B) Molecular weight: the molecular weight of the polypeptide chain portion of the protein measured by SDS-polyacrylamide electrophoresis is 65000;

(C) Thermal stability: the residual activity after treatment at 60° C. for 15 minutes is 85% or more, the residual activity after treatment at 65° C. for 15 minutes is 50% or more, and the residual activity after treatment at 70° C. for 15 minutes is 10% or more;

(D) Optimum reaction pH: 7.0; and (E) Substrate specificity:

the reactivity to maltose is 2% or less based on the reactivity to D-glucose taken as 100%, the reactivity to D-galactose is 2% or less based on the reactivity to D-glucose taken as 100%, and the reactivity to D-xylose is 10% or less based on the reactivity to D-glucose taken as 100%.

The enzyme activity of FAD-GDH is measured by the method described later in the "FAD-GDH Activity Measurement Method" section.

(1-1) Thermal Stability

In the present specification, thermal stability is evaluated by activity maintained even after performing heat treatment for 15 minutes in the state in which 2 U/ml of GDH is contained in a 0.1 M potassium phosphate buffer (pH of 6.0).

The residual activity of the FAD-GDH of the present invention after heating at 60° C. for 15 minutes is 85% or more, preferably 90% or more, and even more preferably 95% or more.

Moreover, the residual activity of the FAD-GDH of the present invention after heat treatment at 65° C. for 15 minutes is 50% or more, preferably 60% or more, and even more preferably 70% or more.

Further, the residual activity of the FAD-GDH of the present invention after treatment at 70° C. for 15 minutes is 10% or more, preferably 20% or more, and even more preferably 30% or more.

(1-2) Substrate Specificity

In the present specification, substrate specificity is evaluated as described later in the "Method for Evaluating Substrate Specificity" section.

The FAD-GDH of the present invention has reactivity to maltose of 2% or less, and preferably 1% or less, based on the reactivity to D-glucose taken as 100%.

The FAD-GDH of the present invention also has reactivity to D-galactose of 2% or less, and preferably 1% or less, based on the reactivity to D-glucose taken as 100%.

The FAD-GDH of the present invention further has reactivity to D-xylose of 1.0% or less, and preferably 5% or less, based on the reactivity to D-glucose taken as 100%.

(1-3) Molecular Weight

In the present specification, "the molecular weight of the polypeptide chain portion of the protein" is a molecular weight estimated by performing SDS-PAGE after removing the sugar chain portion with endoglycosidase H. (More precisely, after removing the sugar chain portion, one N-acetylglucosamine remains in an asparagine residue on the polypeptide chain with a sugar chain originally added thereto).

The molecular weight of the polypeptide chain portion of the FAD-GDH protein of the present invention is about 65000.

The molecular weight of the polypeptide chain portion of the FAD-GDH protein of the present invention measured by SDS-PAGE is generally 60 to 70 kDa. "60 to 70 kDa" includes a range in which a person skilled in the art would usually determine that the band is present at a position between 60 kDa and 70 kDa when a molecular weight is measured by SDS-PAGE.

The molecular weight measurement by SDS-PAGE can be performed using general techniques and devices with the use of commercially available molecular weight markers.

(1-4) Optimum Reaction pH

In the present specification, the optimum reaction pH is evaluated in the following manner.

Measurement liquids having various pHs ranging from 5.0 to 9.0 are prepared using buffers instead of 0.1 mol/L HEPES in the composition of the reaction liquid described later in the "FAD-GDH Activity Measurement Method" section.

Subsequently, the FAD-GDH activity at each pH is measured using each measurement liquid according to the procedure described in the "Activity Measurement Method" section.

Based on the results, the relative activity value at each pH is calculated with the activity value at conditions showing the highest activity taken as 100.

The optimum reaction pH in the FAD-GDH of the present invention is 7.0.

From another viewpoint, a preferred embodiment of the present invention is FAD-GDH having the following properties (A) to (C):

(A) Amino acid sequence: the FAD-GDH has an amino acid sequence with 78% or more identity to the amino acid sequence of SEQ ID NO: 3;

(B) Action: the FAD-GDH catalyzes a reaction in which D-glucose is oxidized in the presence of an electron acceptor to produce D-glucono-δ-lactone; and (C) Thermal stability: the residual activity after treatment at 60° C. for 15 minutes is 85% or more, the residual activity after treatment at 65° C. for 15 minutes is 50% or more, and the residual activity after treatment at 70° C. for 15 minutes is 10% or more.

(1-5) Amino Acid Sequence

The FAD-GDH of the present invention has an amino acid sequence with 78% or more, preferably 85% or more, more preferably 90% or more, even more preferably 95% or more, still even more preferably 98% or more, further preferably 99% or more, and the most preferably 100% (the same as SEQ ID NO: 3) identity to the amino acid sequence of SEQ ID NO: 3 insofar as it has the action of (B) and the thermal stability of (C).

From another viewpoint, the FAD-GDH of the present invention may have the amino acid sequence of SEQ ID NO: 3 in which one or more amino acid residues are substituted, deleted, inserted, and/or added insofar as it has the action of (B) and the thermal stability of (C).

In one embodiment, the FAD-GDH comprises a polypeptide which does not have the amino acid sequence of SEQ ID NO: 3 on order to possess an improved characteristics compared to the Wild type enzyme having the amino acid sequence of SEQ ID NO:3.

The amino acid sequence of SEQ ID NO: 3 is the amino acid sequence of FAD-GDH derived from *Aspergillus* sp. RD009469, as shown in the Examples described later.

Various methods are known for calculating the amino acid sequence identity. For example, the amino acid sequence identity can be calculated using a commercially available analytical tool or an analytical tool available through telecommunication lines (Internet).

In the present specification, the amino acid sequence identity is calculated using parameters with default (initial) settings in the homology algorithm BLAST (basic local alignment search tool) of the National Center for Biotechnology Information (NCBI) (http://www.ncbi.nlm.nih.gov/BLAST/).

The signal peptide portion may be deleted in the polypeptide of the FAD-GDH. According to estimation using SignalP 4.1, position 1 to position 16 in the amino acid sequence of SEQ ID NO: 3 are predicted to be a signal sequence. Therefore, it is inferred that deletion of this portion will not have a negative effect on the enzymatic properties.

(1-6) Origin

The origin of the FAD-GDH of the present invention is not particularly limited. The FAD-GDH of the present invention is preferably derived from a filamentous fungus, more preferably the genus *Aspergillus*, and the most preferably strain owned by National Institute of Technology and Evaluation as *Aspergillus* sp. RD009469 strain.

(2) Method for Producing FAD-GDH

Another embodiment of the present invention is a method for producing the FAD-GDH described above, the method comprising culturing, in a nutrient Medium, a microorganism that produces the FAD-GDH and collecting a protein having glucose dehydrogenase activity.

The FAD-GDH of the present invention can be produced by culturing a strain from which the GDH of the present invention is derived. The FAD-GDH of the present invention can also be produced by culturing a transformant obtained by obtaining DNA encoding the FAD-GDH of the present invention and transforming the DNA into a suitable host.

An example of the method for producing a plasmid capable of expressing DNA encoding the FAD-GDH of the present invention is a method in which a strain from which the FAD-GDH of the present invention is derived is cultured, genomic DNA or total RNA is extracted from the obtained cells, and a cDNA library is prepared according to a standard method.

For example, in the case of genomic DNA, the full length of the gene can be cloned by inverse PCR, and in the case of cDNA library, the full length of the gene can be cloned by determining the terminus sequences by 5'-RACE and 3'-RACE. The most preferable example of the DNA sequence encoding the FAD-GDH thus obtained is the base sequence of SEQ ID NO: 2.

(2-1) DNA Encoding FAD-GDH

Examples of the DNA sequence encoding the FAD-GDH of the present invention include (a) the base sequence of SEQ ID NO: 2 described above, and also include the following (b) to (f):

(b) DNA encoding the amino acid sequence of SEQ ID NO: 3;

(c) DNA having a base sequence with 80% or more homology to the base sequence of SEQ ID NO: 2, and encoding a polypeptide having FAD-GDH activity;

(d) DNA hybridizing to a base sequence complementary to the base sequence of SEQ ID NO: 2 under stringent conditions, and encoding a polypeptide having FAD-GDH activity;

(e) DNA having the base sequence of SEQ ID NO: 2 in which one or more bases are substituted, deleted, inserted, added, and/or inverted, and encoding a polypeptide having FAD-GDH activity; and (f) DNA encoding the amino acid sequence of SEQ ID NO: 3 in which one or more amino acid residues are substituted, deleted, inserted, and/or added, and encoding a polypeptide having FAD-GDH activity.

As used herein, the phrase "DNA encoding a protein" refers to DNA from which the protein is obtained when the DNA is expressed. Specifically, "DNA encoding a protein" refers to DNA having a base sequence corresponding to the amino acid sequence of the protein. Therefore, "DNA encoding a protein" also includes DNA that varies according to codon degeneracy.

The DNA of the present invention has a base sequence with 80% or more, preferably 85% or more, more preferably 88% or more, even more preferably 90% or more, still even more preferably 93% or more, further preferably 95% or more, further more preferably 98% or more, and further even more preferably 99% or more identity to the base sequence of SEQ ID NO: 2 insofar as the protein having the amino acid sequence encoded by this DNA has FAD-GDH activity.

Various methods are known for calculating the base sequence identity. For example, the base sequence identity can be calculated using a commercially available analytical tool or an analytical tool available through telecommunication lines (Internet).

In the present specification, the homology value (%) of a nucleotide sequence is calculated by using a blastn program and setting the parameters to default values to perform a search in homology algorithm Advanced BLAST 2.1 of the National Center for Biotechnology Information (NCBI).

The DNA of the present invention may be DNA hybridizing to a base sequence complementary to the base sequence of SEQ ID NO: 2 under stringent conditions insofar as the protein encoded by this DNA has FAD-GDH activity.

"Stringent conditions" as used herein refer to the following conditions.

50% formamide, 5×SSC (0.15 M NaCl, 15 mM sodium citrate, pH of 7.0), 1×Denhardt's solution, 1% SDS, 10% dextran sulfate, 10 µg/mL of denatured salmon sperm DNA, and 50 mM phosphate buffer (pH of 7.5) are used at 65° C. as an hybridization liquid.

DNA that undergoes hybridization under the above conditions possibly includes DNA containing a stop codon in the middle, or DNA whose activity is abolished as a result of the mutation in the active center. However, such DNA can be easily removed by introducing it into a commercially available active expression vector, expressing it in a suitable host, and determining the enzyme activity using known techniques.

As a method for obtaining the DNA used for the production of the FAD-GDH of the present invention, it is possible to construct DNA encoding the full length of the FAD-GDH of the present invention by chemically synthesizing a DNA chain, or by ligating synthetic oligo DNA short-chains partially overlapping with each other by PCR. The advantage of the construction of the full-length DNA by a combination of chemical synthesis and/or PCR is that it enables designing codons for the full length of the gene according to a host to which the gene is introduced. Since the codon usage frequency varies for each organism species, the multiple codons encoding the same amino acid are not evenly used. Genes highly expressed in an organism species usually contain a large number of codons frequently used in the organism species. Conversely, if the expression amount of a certain gene is low, the presence of infrequently used codons often prevents the gene from being highly expressed. There are many reports of successful increase in an expression amount of a gene of heterologous protein by substituting the gene sequence with codons frequently used in the host organism. Accordingly, such a modification of codons used is expected to increase the expression amounts of heterologous genes.

For this reason, it is desired to modify the codons of the DNA encoding the FAD-GDH of the present invention into codons more suitable for host cells to which the DNA is introduced (i.e., codons frequently used in the host). The codon usage frequency of a host is defined as the usage frequency of each codon in all the genes in the genome sequence of the host organism. For example, the codon usage frequency is expressed based on usage frequency per 1,000 codons. For an organism whose entire genome sequence is yet unknown, the codon usage frequency can be approximately calculated from the sequences of representative genes of the organism. The data of codon usage frequency in a host organism subjected to recombination may be obtained using, for example, the genetic code usage frequency database on the website of the Kazusa DNA Research Institute (http://www.kazusa.or.jp). The data of codon usage frequency in the host organism may also be obtained by referring to documents disclosing codon usage frequencies of various organisms, or the user may determine the codon usage frequency data for the host organism to be used. By referring to the obtained data and the gene sequence to be introduced, the codons in the gene sequence that are less frequently used in the host organism may be replaced by frequently used codons encoding the same amino acid. For example, if the host is K12-strain of *Escherichia coli*, examples of such frequently used codons include GGT or GGC for Gly, GAA for Glu, GAT for Asp, GTG for GCG for Ala, CGT or CGC for Arg, AGC for Ser, AAA for Lys, ATT or ATC for Ile, ACC for Thr, CTG for Leu, CAG for Gln, CCG for Pro, and the like.

(2-2) Host-Vector System

The DNA encoding the FAD-GDH of the present invention is transformed in the state that it is ligated to a recombinant vector. As the recombinant vector of the present invention, a recombinant vector capable of replication retention or autonomous proliferation in various prokaryotic and/or eukaryotic host cells is preferably selected. Examples include plasmid vectors, virus vectors, and the like. The recombinant vector may be simply prepared by ligating the DNA encoding the FAD-GDH into a known cloning or expression vector available in the art using an appropriate restriction enzyme and ligase, or, if necessary, linker or adaptor DNA. If the DNA encoding the FAD-GDH is a gene fragment amplified using a DNA polymerase that adds a base to the amplification terminus, such as Taq polymerase, it may be ligated into a vector by TA cloning. When the DNA is introduced into the genomic DNA of a host cell, the vector is not necessarily capable of replication retention or autonomous proliferation in the host cell; the vector may have at least a gene encoding the GDH of the present invention, a promoter operable in the host cell, and a marker gene for transformant selection; and the gene recombination system inherent in the host cell may be used or the vector may be introduced into the host cell together with endonuclease gene etc. that is necessary to insert the gene into the genomic DNA, and transformants into which the desired DNA is inserted may be selected.

Examples of vectors include *Escherichia-coli*-derived plasmids such as pBR322, pBR325, pUC18, and pUC19; yeast-derived plasmids, such as pSH19 and pSH15; *Bacillus-subtilis*-derived plasmids, such as pUB110, pTP5, and pC194; and the like. Further, examples of viruses include bacteriophages, such as λphage; papovaviruses, such as SV40 and bovine papilloma virus (BPV); retroviruses, such as Moloney murine leukemia virus (MoMuLV); and animal and insect viruses, such as adenovirus (AdV), adeno-associated virus (AAV), vaccinia virus, and baculovirus.

In particular, the present invention provides an FAD-GDH expression vector in which the DNA encoding FAD-GDH is under control of a functional promoter in the target host cells. The vector is not particularly limited insofar as it is a vector that functions in various prokaryotic and/or eukaryotic host cells, and has a promoter region that controls the transcription of the downstream gene, and a transcription termination signal, i.e., a terminator region, of the gene, and insofar as the promoter region and the terminator region are connected via a sequence including at least one restriction enzyme recognition site, more preferably a unique restriction site that cleaves the vector only at the target portion. Examples of promoter regions include, in the case of *Escherichia coli* host cells, trp promoter, lac promoter, lecA promoter, and the like; in the case of *Bacillus subtilis* host cells, SPO1 promoter, SPO2 promoter, penP promoter, and the like; in the case of yeast host cells, PHO5 promoter, PGK promoter, GAP promoter, ADH promoter, and the like; and in the case of mammalian host cells, virus promoters such as SV40-derived early promoter, MoMuLV-derived long terminal repeat, and adenovirus-derived early promoter. The vector preferably further contains a selectable marker gene for transformant selection (such as genes imparting resistance to drugs such as tetracycline, ampicillin, kanamycin, hygromycin, and phosphinothricin and genes complementary to an auxotrophic mutation). Further, when the DNA encoding GDH to be inserted does not contain a start codon or a stop codon, it is preferable to use a vector containing a start codon (ATG or GTG) and a stop codon (TAG, TGA, TAA) in the downstream of the promoter region and the upstream of the terminator region, respectively.

When a bacterium is used as a host cell, generally, the expression vector needs to include a replicable unit that can undergo autonomous replication in the host cells, in addition to the promoter region and the terminator region. Further, the promoter region includes an operator and a Shine-Dalgarno (SD) sequence in the vicinity of the promoter.

When yeast, an animal cell, or an insect cell is used as a host cell, the expression vector preferably further includes an enhancer sequence, 5' and 3' untranslated regions of GDH mRNA, a polyadenylation site, and the like.

(2-3) Production of FAD-GDH

The FAD-GDH of the present invention can be produced by culturing a transformant containing the FAD-GDH expression vector prepared in the above manner in a medium and collecting GDH from the obtained culture.

The medium used preferably contains a carbon source or an inorganic or organic nitrogen source required for the growth of host cells (organism from which the FAD-GDH of the present invention is derived, or transformant). Examples of carbon sources include glucose, dextran, soluble starch, sucrose, and the like. Examples of inorganic or organic nitrogen sources include ammonium salts, nitric acid salts, amino acids, corn steep liquors, peptones, caseins, meat extracts, soybean cakes, potato extracts, and the like. The medium may contain, as desired, other nutrients such as inorganic salts (e.g., calcium chloride, sodium dihydrogen phosphate, and magnesium chloride), vitamins, and antibiotics (e.g., tetracycline, neomycin, ampicillin, kanamycin, and the like).

The culture is performed by using a method known in the art. Specific media and culture conditions used according to host cells are given below as examples; however, the culture conditions of the present invention are not limited to these media and conditions.

When the host is bacteria, actinomycetes, yeast, filamentous fungi, or the like, for example, liquid media containing the above nutrient sources are suitable. The medium preferably has a pH of 5 to 9. When the host is *Escherichia coli*, examples of preferable media include LB medium, M9 medium (Miller. J., Exp. Mol. Genet, p.431, Cold Spring Harbor Laboratory, New York (1972)), and the like. The culture can be generally performed at 14 to 43° C. for about 3 to 72 hours, and if necessary, with aeration and/or agitation. When the host is *Bacillus subtilis*, the culture can be generally performed at 30 to 40° C. for about 16 to 96 hours, and if necessary, with aeration and/or agitation. When the host is yeast, examples of media include Burkholder minimal medium (Bostian. K. L. et al, Proc. Natl. Acad. Sci. USA, 77, 4505 (1980)). The medium preferably has a pH of 5 to 8. The culture is generally performed at about 20 to 35° C. for about 14 to 144 hours, and if necessary, aeration and/or agitation can also be performed.

When the host is an animal cell, examples of media include minimal essential medium (MEM) containing about 5 to 20% fetal bovine serum (Science, 122, 501 (1952)), Dulbecco's modified Eagle's medium (DMEM) (Virology, 8, 396 (1959)), RPMI1640 medium (J. Am. Med. Assoc., 199, 519 (1967)), 199 medium (Proc. Soc. Exp. Biol. Med., 73, 1 (1950)), and the like. The medium preferably has a pH of about 6 to 8. The culture is generally performed at about 30 to 40° C. for about 15 to 72 hours, and if necessary, aeration and/or agitation can also be performed.

When the host is an insect cell, examples of media include Grace's medium containing fetal bovine serum (Proc. Natl. Acad. Sci. USA, 82, 8404 (1985)) and the like. The medium preferably has a pH of about 5 to 8. The culture is generally performed at about 20 to 40° C. for about 15 to 100 hours, and if necessary, aeration and/or agitation can also be performed.

The purification of GDH can be performed by combining various general isolation techniques according to the fraction in which the GDH activity is present.

GDH in the medium of the culture may be obtained by centrifuging or filtering the culture to obtain a culture supernatant (filtrate), and isolating GDH from the culture supernatant using a known isolation method suitably selected from, for example, salting out, solvent precipitation, dialysis, ultrafiltration, gel filtration, nondenaturing PAGE, SDS-PAGE, ion-exchange chromatography, hydroxylapatite chromatography, affinity chromatography, reverse-phase high-performance liquid chromatography, isoelectric focusing, and the like.

GDH in the cytoplasm may be isolated and purified by centrifuging or filtering the culture to collect cells; suspending the cells in an appropriate buffer; disrupting (lysing) the cells and the organelle membrane using, for example, ultrasonic treatment, lysozyme treatment, freezing and thawing, osmotic shock, and/or treatment using a surfactant such as Triton X-100; removing debris by centrifugation or filtration to obtain a soluble fraction; and treating the soluble fraction in the same manner as described above.

A preferable example of a rapid and simple means of obtaining recombinant GDH is a method in which a DNA sequence encoding an amino acid sequence capable of adsorbing to a metal ion chelate (for example, a sequence of a basic amino acid such as histidine, arginine, or lysine, preferably a sequence of histidine)("tag") is added to a portion having the coding sequence of GDH (preferably N or C terminus) using genetic engineering technology; the resulting material is expressed in host cells; and GDH is isolated and collected from the GDH activity fraction of the cultured cells using affinity with the carrier on which the metal ion chelate is immobilized.

The DNA sequence encoding an amino acid sequence capable of adsorbing to a metal ion chelate can be introduced into the GDH cording sequence, for example, through PCR amplification using a hybrid primer obtained by connecting the DNA sequence to a base sequence encoding the amino acid sequence of C terminus of the GDH during the step of cloning DNA encoding the GDH, or through in-frame insertion of the DNA encoding the GDH into an expression vector that includes the DNA sequence before the stop codon. Further, the metal ion chelate adsorbent used for the purification is prepared by bringing a solution containing a transition metal such as bivalent ions of cobalt, copper, nickel and iron, or trivalent ions of iron and aluminum, preferably bivalent ion of cobalt or nickel, into contact with a matrix to which a ligand, such as an iminodiacetic acid (IDA) group, a nitrilotriacetic acid (NTA) group, a tris (carboxymethyl) ethylene diamine (TED) group, or the like, is attached, thereby inducing the bond with the ligand. The matrix portion of the chelate adsorbent is not particularly limited insofar as it is a general insoluble carrier.

Alternatively, the purification can be performed through affinity purification using glutathione-S-transferase (GST), maltose-binding protein (MBP), HA, FLAG peptide, or the like as a tag.

During the above purification step, membrane concentration, concentration under reduced pressure, addition of an activator and a stabilizer, or the like may be performed, if necessary. Since the GDH of the present invention has excellent heat resistance, heat treatment that heat-denatures contaminating proteins derived from other host cells, and that allows the GDH activity to be retained is especially effective for significantly enhancing the GDH purity. Although the solvents used in these steps are not particularly limited, they are preferably buffers having a buffering ability at a pH of about 6 to 9, such as K-phosphate buffer, Tris-HCl buffer, and Good's buffer.

When the thus-obtained GDH is a free body, it may be converted into a salt by using a method known per se or a similar method. When the protein is obtained as a salt, it may be converted into a free body or another salt using a method known per se or a similar method.

Moreover, a stabilizer and/or an activator may be suitably added to a solution or composition containing the GDH. Examples of stabilizers and activators include bovine serum albumin, sericin, and like proteins; Triton X-100, Tween 20, cholic acid salts, deoxycholic acid salts, and like surfactants; glycine, serine, glutamic acid, glutamine, aspartic acid, asparagine, glycylglycine, and like amino acids; trehalose, inositol, sorbitol, xylitol, glycerol, sucrose, mannitol, and like sugars and/or sugar alcohols; sodium chloride, potassium chloride, and like inorganic salts; and pullulan, dextran, polyethylene glycol, polyvinylpyrrolidone, carboxymethylcellulose, polyglutamic acid, and like hydrophilic polymers.

The purified enzyme may be provided as an industrial material in liquid form, or may be powdered or granulated. The powderization of the liquid enzyme is performed using an ordinary freeze-drying method.

Furthermore, the GDH of the present invention can also be synthesized through in vitro translation using a cell-free protein translation system containing a rabbit reticulocyte lysate, a wheat germ lysate, an *Escherichia coli* lysate, or the like by using RNA corresponding to DNA encoding the GDH as a template. The RNA encoding the GDH of the present invention can be obtained either by purifying mRNA encoding the GDH of the present invention from host cells in which the RNA is expressed using a standard method as described above in the method for obtaining cDNA encoding the GDH of the present invention, or by preparing cRNA using a cell-free transcription system containing RNA polymerase using DNA encoding the GDH as a template. The cell-free protein transcription/translation system may be a commercially available cell-free protein transcription/translation system, or may be prepared using a method known per se. More specifically, an *Escherichia coli* extract may be prepared according to the method disclosed in, for example, Pratt J. M. et al., "Transcription and Translation", Hames B. D. and Higgins S. J. eds., IRL Press, Oxford 179-209 (1984). Examples of commercially available cell lysates include *Escherichia-coli*-derived cell lysates, such as *E. coli* S30 extract system (produced by Promega) and RTS 500 Rapid Translation System (produced by Roche), rabbit-reticulocyte-derived cell lysates, such as Rabbit Reticulocyte Lysate System (produced by Promega), wheat-germ-derived cell lysates, such as PROTEIOS™ (produced by TOYOBO), and the like. Among these, wheat germ lysates are preferable. Wheat germ lysates can be produced, for example, using the method disclosed in, for example, Johnston F. B. et al., Nature, 179: 160-161 (1957), or Erickson A. H. et al., Meth. Enzymol., 96: 38-50 (1996).

The production of GDH through chemical synthesis can be performed, for example, by synthesizing all or a portion of its sequence based on the amino acid sequence of SEQ ID NO: 3, i.e., the amino acid sequence of the GDH of the present invention, using a peptide synthesizer. The peptide synthesis method may, for example, be solid-phase synthesis or liquid-phase synthesis. The protein of interest can be produced by condensation of a partial peptide or amino acids that can constitute the GDH of the present invention and the remaining portion. When the resulting product contains a protecting group, the protecting group is eliminated. The condensation and the elimination of a protecting group are performed according to methods known per se, such as the methods disclosed in the following documents (1) and (2):

(1) M. Bodanszky and M. A. Ondetti, Peptide Synthesis, Interscience Publishers, New York (1966), (2) Schroeder and Luebke, The Peptide, Academic Press, New York (1965).

The GDH of the present invention thus obtained can be isolated and purified by a known purification method. Examples of purification methods include solvent extraction, distillation, column chromatography, liquid chromatography, recrystallization, and combinations of these methods.

When the thus-obtained GDH is a free body, it may be converted into an appropriate salt by using a known method or a similar method. Conversely, when the protein is obtained as a salt, it may be converted into a free body or another salt using a known method or a similar method.

(3) Method for Measuring Glucose and the Like

Another embodiment of the present invention is use of the FAD-GDH of the present invention, which has the properties described above. An example of the use is a method for measuring glucose. The FAD-GDH of the present invention can be suitably used, for example, for measuring blood glucose levels or measuring the glucose concentration in food (such as seasonings and beverages).

Yet another embodiment of the present invention is various products for measuring glucose, such as glucose assay kits and glucose sensors. The products comprise the FAD-GDH of the present invention, which has the properties described above.

Methods for measuring glucose using FAD-GDH have already been established in the art. Thus, the amount or concentration of Glucose in various samples can be measured using the FAD-GDH of the present invention according to known methods. The mode for the measurement is not particularly limited, as long as the amount or concentration of glucose can be measured by using the FAD-GDH of the prevent invention.

(3-1) Reagent for Measuring Glucose

The reagent for measuring glucose of the present invention typically comprises the GDH of the present invention, a buffer, a glucose standard solution for preparing a calibration curve, and instructions for use. The reagent also preferably comprises a reagent necessary for the measurement such as a mediator. Moreover, a stabilizer and/or an activator may be suitably added to the reagent comprising the GDH. Examples of stabilizers and activators include bovine serum albumin, sericin, and like proteins; Triton X-100, Tween 20, cholic acid salts, deoxycholic acid salts, and like surfactants; glycine, serine, glutamic acid, Glutamine, aspartic acid, asparagine, glycylglycine, and like amino acids; trehalose, inositol, sorbitol, xylitol, glycerol, sucrose, mannitol, and like sugars and/or sugar alcohols; sodium chloride, potassium chloride, and like inorganic salts; and pullulan, dextran, polyethylene glycol, polyvinylpyrrolidone, carboxymethylcellulose, polygiutamic acid, and like hydrophilic polymers.

(3-2) Glucose Assay Kit

The glucose assay kit of the present invention typically comprises the GDH of the present invention, a buffer, a reagent necessary for the measurement such as a mediator, a glucose standard solution for preparing a calibration curve, and instructions for use. The kit of the present invention may be provided as, for example, a freeze-dried reagent or a solution in an appropriate storage solution. Moreover, a stabilizer and/or an activator may be suitably added to the reagent comprising the GDH. Examples of stabilizers and activators include bovine serum albumin, sericin, and like proteins; Triton X-100, Tween 20, cholic acid salt, deoxycholic acid salt, and like surfactants; glycine, serine, glutamic acid, glutamine, aspartic acid, asparagine, glycylglycine, and like amino acids; trehalose, inositol, sorbitol, xylitol, glycerol, sucrose, and like sugars and/or sugar alcohols; sodium chloride, potassium chloride, and like inorganic salts; and pullulan, dextran, polyethylene glycol, polyvinylpyrrolidone, carboxymethylcellulose, polyglutamic acid, and like hydrophilic polymers.

(3-3) Glucose Sensor

In the Glucose sensor of the present invention, the GDH is immobilized on an electrode, such as a carbon electrode, a gold electrode, or a platinum electrode. Examples of immobilization methods include a method using a crosslinking reagent, a method for encapsulating the GDH in a polymer matrix, a method for covering the GDH with a dialysis membrane, and methods using a photo-crosslinkable polymer, a conductive polymer, a redox polymer, or the like. Alternatively, the GDH may be immobilized in a polymer or immobilized adsorptively onto an electrode, together with a coenzyme such as NAD or NADP, or an electron mediator. These methods may also be used in combination. Typically, the GDH of the present invention is immobilized on a carbon electrode using glutaraldehyde, followed by treatment with an amine-containing reagent to block the glutaraldehyde. Examples of the electron mediator used include those that can receive electrons from FAD, which is a coenzyme of GDH, and donate electrons to a coloring substance or an electrode. Examples include, but are not limited to, ferricyanide salt, phenazine ethosulfate, phenazine methosulfate, phenylenediamine, N,N,N',N'-tetramethylphenylenediamine, 1-methoxy-phenazine methosulfate, 2,6-dichlorophenolindophenol, 2,5-dimethyl-1,4-benzoquinone, 2,6-dimethyl-1,4-benzoquinone, 2,5-dichloro-1,4-benzoquinone, nitrosoaniline, ferrocene derivatives, osmium complexes, ruthenium complexes, and the like. Moreover, the GDH composition on the electrode may contain a stabilizer and/or an activator. Examples of stabilizers and activators include bovine serum albumin, sericin, and like proteins; Triton X-100, Tween 20, cholic acid salt, deoxycholic acid salt, and like surfactants; glycine, serine, glutamic acid, glutamine, aspartic acid, asparagine, glycylglycine, and like amino acids; trehalose, inositol, sorbitol, xylitol, glycerol, sucrose, and like sugars and/or sugar alcohols; sodium chloride, potassium chloride, and like inorganic salts; and pullulan, dextran, polyethylene glycol, polyvinylpyrrolidone, carboxymethylcellulose, polyglutamic acid, and like hydrophilic polymers.

The glucose concentration can be measured in the following manner. A reaction liquid containing a buffer, GDH, and 2,6-dichlorophenolindophenol (DCPIP) as a mediator is placed in a thermostated cell, and a constant temperature is maintained. A sample containing glucose is added thereto, and a reaction is performed at a constant temperature for a certain period of time. Glucose can be quantified by monitoring a decrease in absorbance at 600 nm during this time. Alternatively, the glucose concentration can be determined by adding phenazine methosulfate (PMS) as a mediator, and nitrotetrazorium blue (NTB) as a coloring reagent, and by measuring the absorbance at 570 nm, thereby determining the amount of diformazan produced. The mediator and coloring reagent used are by no means limited to those mentioned above.

The glucose concentration can also be measured in the following manner. A buffer is placed in a thermostated cell. GDH and, if necessary, a mediator are added thereto, and a constant temperature is maintained. Potassium ferricyanide, phenazine rnethosulfate, or the like, can be used as a mediator. An electrode on which the GDH of the present invention is immobilized is used as a working electrode, and a counter electrode (e.g., a platinum electrode) and a reference electrode (e.g., an AG/AgCl electrode) are used. A constant voltage is applied across the carbon electrode. After the current becomes constant, a sample containing glucose is added, and an increase in current is measured. The Glucose concentration in the sample can be calculated based on a calibration curve prepared from glucose solutions of standard concentration.

(4) Measurement Method and the Like (4-1) FAD-GDH Activity Measurement Method

In the present specification, the FAD-GDH activity is measured according to the following method, unless otherwise stated.

2.9 mL of a reaction liquid (0.1 mol/L HEPES, 200 mmol/L D-glucose, 0.55 mmol/L DCPIP, pH of 6.5) is placed in a quartz cell, and pre-heated at 37° C. for 5 minutes. 0.1 mL of a GDH solution is added and mixed with the reaction liquid, and a reaction is carried out at 37° C. for 5 minutes. During the reaction, the absorbance at 700 nm is measured. An increase in absorbance per minute ($\Delta OD_{TEST}$) is calculated from the linear portion of the change in absorbance. In a blind test, a buffer is added instead of the GDH solution and mixed with the reaction liquid. In the same manner as above, the mixture is incubated at 37° C. for 5 minutes, the absorbance at 700 nm is recorded, and a change in absorbance per minute ($\Delta OD_{BLANK}$) is calculated. These values are applied in the following equation to calculate the activity value (U/mL). Here, the amount of enzyme that reduces 1 micromole of DCPIP per minute in the presence of a substrate is defined as 1 U.

$$\text{GDH activity (U/mL)} = [(\Delta OD_{TEST} - \Delta OD_{BLANK}) \times 3.0 \times \text{dilution factor}]/(4.5 \times 1.0 \times 0.1)$$

wherein 3.0: volume (mL) of the mixture after addition of the GDH solution, 4.5: millimolar molecular absorption coefficient ($cm^2$/micromole) of DCPIP 1.0: optical path length (cm)

0.1: liquid amount (mL) of the GDH solution added (4-2) Examples of Protein Quantification and Specific Activity Calculation The protein amount in the present invention is determined by measuring the absorbance at 280 nm. Specifically, an enzyme solution is diluted with distilled water so that the absorbance at 280 nm falls within a range of 0.1 to 1.0, and the absorbance at 280 nm (Abs) is measured with an absorption spectrometer adjusted to the zero point using distilled water. The protein concentration in the present invention is approximately in the relation of 1 Abs≈1 mg/ml, and obtained by multiplying the result by the measured absorbance and the dilution factor of the measured solution. Further, the specific activity of the present invention refers to GDH activity (U/mg) per mg of a protein amount measured by the above method. The GDH activity is measured by the method described in the activity measurement example above.

(4-3) Example of Calculation of Michaelis Constant (KM) for Glucose

The Michaelis constant (Km) for a substrate in the present invention is calculated in the following manner. Specifically, prepared as measurement solutions are five reaction liquids whose D-glucose concentrations are respectively 200 mmol/L, 160 mmol/L, 120 mmol/L, 80 mmol/L, and 40 mmol/L in the composition of the reaction liquid described in the activity measurement example above. $\Delta OD$ ($\Delta OD_{TEST} - \Delta OD_{BLANK}$) of a GDH solution (a solution adjusted so that the activity value in the activity measurement example above is 0.8 U/ml) is determined using the measurement solutions according to the method described in the activity measurement example above. Based on the thus-obtained measurement values, the Michaelis constant (Km) is calculated according to the Lineweaver-Burk plot method (double reciprocal plot method).

(4-4) Method for Evaluating Substrate Specificity

In the present specification, the substrate specificity is evaluated in the following manner. Specifically, reaction liquids each containing 200 mmol/L of another saccharide (such as maltose, galactose, or xylose) instead of D-glucose in the composition of the reaction liquid described in the "FAD-GDH Activity Measurement Method" section above are individually prepared as measurement solutions. The activity values are measured using these reaction liquids according the method described in the "FAD-GDH Activity Measurement Method" section. The value obtained by dividing each of the activity values obtained using the reaction liquids by the activity value obtained when glucose is used as a substrate is calculated as the reactivity to each substrate (percentage based on reactivity to glucose).

Examples are given below to illustrate the present invention in more detail; however, the present invention is not limited to these Examples.

EXAMPLES

Example 1

Obtaining GDH from the *Aspergillus* sp. RD009469 Strain

The *Aspergillus* sp. RD009469 strain was loaned by the National Institute of Technology and Evaluation. First, this strain was inoculated in an ME agar medium (2% malt extract, 0.1% peptone, 0.1% monopotassium phosphate, 2% glucose, 1.5% agarose, pH of 6.0) and cultured at 25° C. to allow the hypha to grow over the plate. All of the agarose on which the hypha was grown was scraped from the plate and suspended in 100 ml of sterilized water. The agar suspended in 6 L of a YM medium (3% yeast extract, 3% maltose, 0.05% Adeka Nol) was placed in a 10-L jar fermenter, and aeration-agitation culture was performed at 25° C. for 65 hours. After the culture, the GDH activity in the medium supernatant was measured, and activity of 0.2 U/ml was detected. After the culture medium was filtered through filter paper to remove the cells, ammonium sulfate was added in an amount of 300 g per L. After complete dissolution, a 20% sodium hydroxide solution was added to adjust the pH to 6.0. The liquid was passed through a column filled with 200 ml of Phenyl-sepharose (produced by GE Healthcare) and buffered with a 50 mM potassium phosphate buffer (pH of 6.0) containing ammonium sulfate having the same concentration to adsorb GDH. Further, gradient elution was carried out by decreasing the concentration of ammonium sulfate to 0 to elute GDH, and the fractions having GDH activity were collected. Moreover, ultrafiltration was performed using a ultrafiltration membrane (molecular weight cut-off of 10,000) while adding a 50 mM potassium phosphate buffer (pH of 6.0) until the permeated liquid became clear. Finally, gel filtration was performed using a Superdex 200 column (560 ml, produced by GE healthcare) buffered with a 50 mM potassium phosphate buffer (pH of 6.0) containing 300 mM sodium chloride to obtain purified GDH. The specific activity of the obtained purified GDH was about 180 U/mg.

Example 2

Thermal Stability of GDH

The GDH obtained in Example 1 was diluted with a 50 mM potassium phosphate buffer (pH of 6.0) so that the GDH concentration was 2 U/ml. The resulting solutions were subjected to heat treatment for 15 minutes at each temperature from 40° C. to 70° C. in 5° C., increments, and the ratio of the GDH activity after heating to the GDH activity before heating (residual activity) was investigated. FIG. 1 shows the results. The residual activity of the GDH after heating was 94.5% at 60° C., 78.8% at 65° C., and 48.6% at 70° C.

Example 3 pH-Dependence of GDH Activity

Figure 2:
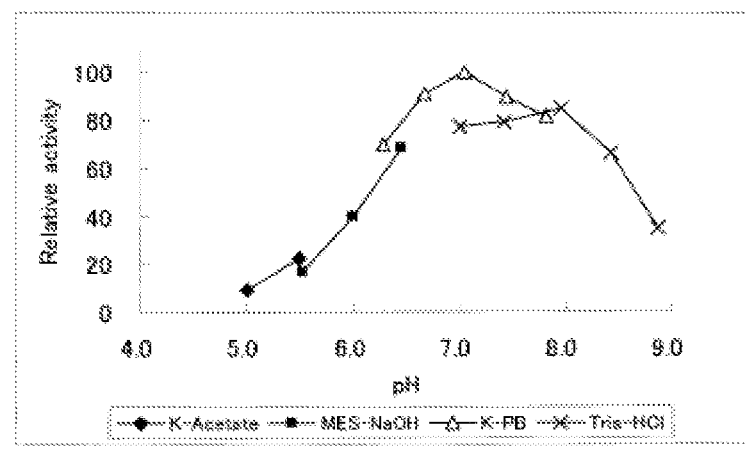
FIG. 2 shows the relative activity of FAD-GDH derived from *Aspergillus* sp. RD009469 strain at each pH.

The pH dependence of GDH activity regarding the GDH obtained in Example 1 was investigated as follows. Measurement liquids having various pHs ranging from 5.0 to 9.0 were prepared by using various buffers instead of 0.1 mol/L HEPES in the composition described in the activity measurement example above. The buffers used were potassium acetate (pH of 5.0 to 5.5), MES-NaOH (pH of 5.5 to 6.5), potassium phosphate (pH of 6.0 to 8.0), and Tris-HCl (pH of 7.0 to 9.0). The concentrations of the buffers in the measurement liquids were all 70 mM. The GDH activity at each pH was measured using each measurement liquid according to the procedure as described in the activity measurement example above. The relative activity at each pH was calculated with the activity value at conditions showing the highest activity taken as 100 (FIG. 2). The optimum reaction pH was about 7.0.

Example 4

Substrate Specificity of GDH

The substrate specificity of the GDH obtained in Example 1 was investigated. The substrate specificity was evaluated according to the method described in the substrate specificity evaluation example above. In addition to maltose, galactose, and xylose, 2-deoxy-D-glucose, fructose, sucrose, mannose, arabinose, glycerol, and melezitose were used as substrates, and the reactivity to these substrates (percentage based on reactivity to glucose) was also measured. Table 1 shows the results. The reactivity to maltose and galactose was less than 1% based on the reactivity to glucose, and the reactivity to xylose was less than 5% based on the reactivity to glucose. The results confirmed that the GDH of the present invention has excellent substrate specificity.

TABLE 1

| Substrate (200 mM) | Relative Activity |
| --- | --- |
| D-Glucose | 100 |
| D-Xylose | 4.1 |
| Maltose | 0.4 |
| D-Galactose | 0.8 |
| D-Mannose | 1.7 |
| 2-Deoxy-D-glucose | 40.8 |
| D-Arabinose | 0.0 |
| D-Fructose | 0.1 |
| D-Melezitose | 1.0 |
| Sucrose | 0.0 |
| Glycerol | 0.0 |

Example 5

Michaelis Constant for a Substrate in GDH

Regarding the GDH obtained in Example 1, the Michaelis constant (Km) for a substrate was determined according to the method described in the calculation example above. The results showed that the Michaelis constant of the GDH of the present invention for D-glucose was 52.2 mM.

Example 6

Estimation of Molecular Weight Using SDS-PAGE and Peptide Mass Analysis

Figure 3:
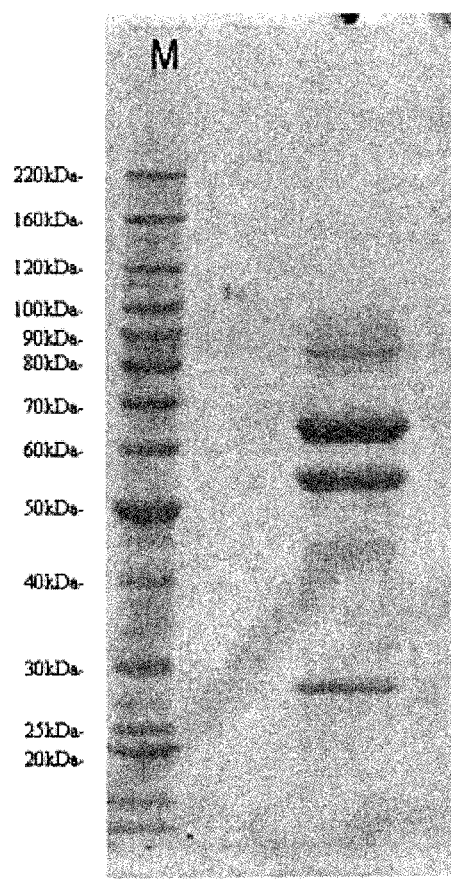
FIG. 3 is an SDS-PAGE gel photograph of the purified FAD-GDH solution obtained in Example 1.

In the GDH obtained in Example 1, the sugar chain was cut with endoglycosidase H (Endo H produced by New England BioLabs), and SDS-PAGE was performed according to a standard method (FIG. 3). Dark bands were observed mainly at 65 kDa and 55 kDa, and the bands were excised from the gel and digested with trypsin. Thereafter, measurement of the molecular weights of the digestion fragments by LC/MS/MS analysis, and protein identification by MASCOT analysis were performed. As a result, the peptide obtained from the band at 65 kDa showed hi hit rate for known FAD-dependent GMC oxidoreductase-like protein, and this band was presumed to be GDH.

Example 7

Estimation of Amino Acid Sequence of GDH

The band at an apparent molecular weight of 65 kDa of SDS-PAGE obtained in Example 6 was excised, subjected to dehydration treatment, and then impregnated with a solution containing trypsin to undergo digestion overnight. The product was subjected to SDS-PAGE and transferred to a PVDF membrane by a semi-dry method, and CBB staining was performed. Some of the bands that appeared were subjected to Edman analysis to determine the N terminus amino acid sequence. Degenerate primers were designed from the obtained sequence, and PCR was performed using cDNA as a template, thereby obtaining a partial fragment of GDH gene. This partial gene fragment was cloned into plasmid pTA2 using a TA-cloning kit produced by Toyobo Co., Ltd. (Target Clone Plus-) to analyze the base sequence. The obtained partial base sequence is shown in SEQ ID NO: 1. Based on this partial sequence information, 5'-RACE and 3'-RACE were further performed according to a standard method to ultimately determine the full-length base sequence encoding the GDH of the present invention. The full-length base sequence encoding the GDH of the present invention is shown in SEQ ID NO: 2. The amino acid sequence of the GDH of the present invention deduced from the base sequence is shown in SEQ ID NO: 3. The identity between this sequence and the sequence in a database was examined, and the results showed that the identity to *Aspergillus terreus* NIH2624-derived hypothetical protein ATEG_08295 (sequence ID: XP_001216916.1) was 77%, which was the highest, followed by the identity to the sequence annotated as *Aspergillus kawachii* IFO4308-derived Glucose oxidase (sequence ID: GAA92291.1) that was 63%. Thus, the GDH of the present invention can be said to be a novel enzyme. The molecular weight of the polypeptide chain estimated by calculation from the above amino acid sequence is 64600, which nearly matches the results of SDS-PAGE shown in Example 6.

INDUSTRIAL APPLICABILITY

Glucose dehydrogenase produced by the present invention can be supplied as a reagent for measuring a blood glucose level, and as a material for a blood glucose sensor and glucose quantification kit.

The invention claimed is:

1. A flavin adenine dinucleotide-dependent glucose dehydrogenase comprising a polypeptide having an amino acid sequence with 85% or more identity to the amino acid sequence of SEQ ID NO: 3, and having glucose dehydrogenase activity, wherein the polypeptide does not comprise the amino acid sequence of SEQ ID NO: 3.

2. The flavin adenine dinucleotide-dependent glucose dehydrogenase according to claim 1, which has the following characteristics (A) to (E):

(A) Action: the flavin adenine dinucleotide-dependent glucose dehydrogenase catalyzes a reaction in which D-glucose is oxidized in the presence of an electron acceptor to produce D-glucono-δ-lactone;

(B) Molecular weight: the molecular weight of the polypeptide chain portion of the protein measured by SDS-polyacrylamide electrophoresis is 65000;

(C) Thermal stability: the residual activity after treatment at 60° C. for 15 minutes is 85% or more, the residual activity after treatment at 65° C. for 15 minutes is 50% or more, and the residual activity after treatment at 70° C. for 15 minutes is 10% or more;

(D) Optimum reaction pH: 7.0; and (E) Substrate specificity:
the reactivity to maltose is 2% or less based on the reactivity to D-glucose taken as 100%,
the reactivity to D-galactose is 2% or less based on the reactivity to D-glucose taken as 100%, and
the reactivity to D-xylose is 10% or less based on the reactivity to D-glucose taken as 100%.

3. The flavin adenine dinucleotide-dependent glucose dehydrogenase according to claim 1, wherein the polypeptide has an amino acid sequence with 90% or more identity to the amino acid sequence of SEQ ID NO: 3.

4. The flavin adenine dinucleotide-dependent glucose dehydrogenase according to claim 1, wherein the polypeptide has an amino acid sequence with 95% or more identity to the amino acid sequence of SEQ ID NO: 3.

5. The flavin adenine dinucleotide-dependent glucose dehydrogenase according to claim 1, wherein the polypeptide has an amino acid sequence with 98% or more identity to the amino acid sequence of SEQ ID NO: 3.

6. The flavin adenine dinucleotide-dependent glucose dehydrogenase according to claim 1, wherein the polypeptide has an amino acid sequence with 99% or more identity to the amino acid sequence of SEQ ID NO: 3.

7. An electrode comprising a flavin adenine dinucleotide-dependent glucose dehydrogenase comprising a polypeptide having an amino acid sequence with 85% or more identity to the amino acid sequence of SEQ ID NO: 3, and having glucose dehydrogenase activity, wherein the flavin-binding glucose dehydrogenase is immobilized onto the electrode.

8. The electrode according to claim 7, which has the following characteristics (A) to (E):

(A) Action: the flavin adenine dinucleotide-dependent glucose dehydrogenase catalyzes a reaction in which D-glucose is oxidized in the presence of an electron acceptor to produce D-glucono-δ-lactone;

(B) Molecular weight: the molecular weight of the polypeptide chain portion of the protein measured by SDS-polyacrylamide electrophoresis is 65000;

(C) Thermal stability: the residual activity after treatment at 60° C. for 15 minutes is 85% or more, the residual activity after treatment at 65° C. for 15 minutes is 50% or more, and the residual activity after treatment at 70° C. for 15 minutes is 10% or more;

(D) Optimum reaction pH: 7.0; and (E) Substrate specificity:
the reactivity to maltose is 2% or less based on the reactivity to D-glucose taken as 100%,
the reactivity to D-galactose is 2% or less based on the reactivity to D-glucose taken as 100%, and
the reactivity to D-xylose is 10% or less based on the reactivity to D-glucose taken as 100%.

9. The electrode according to claim 7, wherein the polypeptide has an amino acid sequence with 90% or more identity to the amino acid sequence of SEQ ID NO: 3.

10. The electrode according to claim 7, wherein the polypeptide has an amino acid sequence with 95% or more identity to the amino acid sequence of SEQ ID NO: 3.

11. The electrode according to claim 7, wherein the polypeptide has an amino acid sequence with 98% or more identity to the amino acid sequence of SEQ ID NO: 3.

12. The electrode according to claim 7, wherein the polypeptide has an amino acid sequence with 99% or more identity to the amino acid sequence of SEQ ID NO: 3.

13. A flavin adenine dinucleotide-dependent glucose dehydrogenase comprising a polypeptide having an amino acid sequence with 85% or more identity to the amino acid sequence of SEQ ID NO: 3, and having glucose dehydrogenase activity, wherein the flavin adenine dinucleotide-dependent glucose dehydrogenase is freeze-dried.

14. The flavin adenine dinucleotide-dependent glucose dehydrogenase according to claim 13, which has the following characteristics (A) to (E):

(A) Action: the flavin adenine dinucleotide-dependent glucose dehydrogenase catalyzes a reaction in which D-glucose is oxidized in the presence of an electron acceptor to produce D-glucono-δ-lactone;

(B) Molecular weight: the molecular weight of the polypeptide chain portion of the protein measured by SDS-polyacrylamide electrophoresis is 65000;

(C) Thermal stability: the residual activity after treatment at 60° C. for 15 minutes is 85% or more, the residual activity after treatment at 65° C. for 15 minutes is 50% or more, and the residual activity after treatment at 70° C. for 15 minutes is 10% or more;

(D) Optimum reaction pH: 7.0; and (E) Substrate specificity:
the reactivity to maltose is 2% or less based on the reactivity to D-glucose taken as 100%,
the reactivity to D-galactose is 2% or less based on the reactivity to D-glucose taken as 100%, and
the reactivity to D-xylose is 10% or less based on the reactivity to D-glucose taken as 100%.

15. The flavin adenine dinucleotide-dependent glucose dehydrogenase according to claim 13, wherein the polypeptide has an amino acid sequence with 90% or more identity to the amino acid sequence of SEQ ID NO: 3.

16. The flavin adenine dinucleotide-dependent glucose dehydrogenase according to claim 13, wherein the polypeptide has an amino acid sequence with 95% or more identity to the amino acid sequence of SEQ ID NO: 3.

17. The flavin adenine dinucleotide-dependent glucose dehydrogenase according to claim 13, wherein the polypeptide has an amino acid sequence with 98% or more identity to the amino acid sequence of SEQ ID NO: 3.

* * * * *